US008075841B2

(12) United States Patent  
Van Herpen et al.

(10) Patent No.: US 8,075,841 B2  
(45) Date of Patent: Dec. 13, 2011

(54) BIOSENSOR WITH ONE-DIMENSIONAL SUB-DIFFRACTION-LIMITED APERTURES COMPOSED OF A GRID AND A POLARIZER

(75) Inventors: Maarten Van Herpen, Heesch (NL); Dirk J. Broer, Geldrop (NL); Emiel Peeters, Eindhoven (NL); Derk J. W Klunder, Geldrop (NL); Hendrik R. Stapert, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 772 days.

(21) Appl. No.: 12/158,347

(22) PCT Filed: Dec. 11, 2006

(86) PCT No.: PCT/IB2006/054750  
§ 371 (c)(1),  
(2), (4) Date: Jun. 20, 2008

(87) PCT Pub. No.: WO2007/072293  
PCT Pub. Date: Jun. 28, 2007

(65) Prior Publication Data  
US 2009/0001284 A1 Jan. 1, 2009

Related U.S. Application Data

(60) Provisional application No. 60/752,083, filed on Dec. 20, 2005.

(51) Int. Cl.  
*G01N 21/64* (2006.01)  
*G01N 21/00* (2006.01)  
*G01J 3/00* (2006.01)  
*G01N 21/76* (2006.01)

(52) U.S. Cl. ... 422/82.08; 422/52; 422/68.1; 422/82.02; 422/82.05; 422/82.06; 422/82.07; 422/82.09; 422/82.11; 422/83; 436/43; 436/63; 436/164; 436/171; 436/172; 250/363.01; 250/458.1; 250/459.1; 356/300; 356/301; 356/303; 356/305

(58) Field of Classification Search .................. None  
See application file for complete search history.

(56) References Cited

U.S. PATENT DOCUMENTS  
5,094,788 A 3/1992 Schrenk  
(Continued)

FOREIGN PATENT DOCUMENTS  
WO 0028327 A1 5/2000  
(Continued)

OTHER PUBLICATIONS

Smalyukh I.I et al "Three-Dimensional Imaging of Orientational Order by Fluorescence Confocal Polarizing Microscopy" Chemical Physics Letters, vol. 336, Mar. 2001, pp. 88-96.  
Schnabel Bernd et al "Study on Polarizing Visible Light by Subwavelength-Period Metal-Stripe Gratings" Opt. Eng. vol. 38, No. 2, Feb. 1999, pp. 220-226.

(Continued)

*Primary Examiner* — Jill Warden  
*Assistant Examiner* — Neil N Turk

(57) ABSTRACT

A method and sensor for the detection of luminescence radiation generated by at least one luminophore is disclosed. In the context of the present invention the biosensor comprises a grid (120) defined as arrays of apertures with the apertures having a first dimension below and a second dimension above the diffraction limit of the excitation light (102) in a medium, a polarizer (115), and luminophores (117) positioned in a volume selected from the group consisting of: the volume inside the apertures of the grid (120), the volume in between the array of slits (120) and the polarizer (115) and a volume that extends into the polarizer (115), wherein the grid (120) providing a transmission axis extending in a first direction and the polarizer (115) providing a transmission axis extending in a second direction, the first direction and the second direction being substantially perpendicular with respect to each other, wherein the excitation radiation (102) is polarized such that it is substantially suppressed by one of the at least one grid (120) and polarizer (115) and substantially not suppressed by the other of the at least one grid (120) and polarizer (115).

18 Claims, 4 Drawing Sheets

U.S. PATENT DOCUMENTS

| | | |
|---|---|---|
| 5,122,905 A | 6/1992 | Wheatley |
| 5,122,906 A | 6/1992 | Wheatley |
| 6,686,208 B2 | 2/2004 | Meusel |
| 2003/0027328 A1 | 2/2003 | Cunningham |
| 2003/0103208 A1 | 6/2003 | Quinn |
| 2003/0203502 A1 | 10/2003 | Zenhausern |
| 2004/0185551 A1 | 9/2004 | Niehaus |
| 2004/0191793 A1 | 9/2004 | Kitawaki |
| 2005/0099622 A1 | 5/2005 | Caracci |
| 2005/0122521 A1 | 6/2005 | Katzlinger |
| 2010/0019155 A1* | 1/2010 | Klunder et al. .......... 250/363.01 |

FOREIGN PATENT DOCUMENTS

| | | |
|---|---|---|
| WO | 2005045485 A1 | 5/2005 |
| WO | 2006136991 A1 | 12/2006 |
| WO | 2007034395 A2 | 3/2007 |

OTHER PUBLICATIONS

Sheppard, C.J.R. et al "An Electromagnetic Theory of Imaging in Fluorescence Microscopy, and Imaging in Polarization Fluorescence Microscopy" Bioimaging No. 5, 1997, pp. 205-218.

* cited by examiner

BIOSENSOR WITH ONE-DIMENSIONAL SUB-DIFFRACTION-LIMITED APERTURES COMPOSED OF A GRID AND A POLARIZER

This application is related to the field of biosensors and more specifically to sub-wavelength biosensors employing an aperture grid and a polarizer.

Biosensor technology is well-known in the art. For example, European Patent Application Serial No. 05105599.4, entitled "Luminescence sensors using sub-wavelength apertures or slits", filed on Jun. 23, 2005, discloses a biosensor with sub-wavelength spatial resolution operating inside a fluid. In simple terms, light is reflected on apertures with at least one transversal dimension below the diffraction limit. This results in an evanescent field within the apertures, which is used for exciting the contained luminophores. The luminescence that is generated exits the apertures on both a reflecting and non-reflecting side, which results in a separation of the excitation radiation from the luminescence radiation at the non-reflecting side. Background luminescence generated on the excitation side of the apertures is also suppressed by the reflection effect.

In the aforementioned patent application, a similar biosensor, employing an array of slits is used in place of apertures. In this case, slits are apertures with a first lateral (i.e., in the plane of the slits) dimension below the diffraction limit and a second lateral dimension above the diffraction limit. The advantage of slits is that the suppression of light becomes polarization-dependent. In this case, the excitation-light can be suppressed by using the correct polarization (electric field is substantially parallel to the first lateral dimension of the slits), while a large portion of the luminescence is not suppressed, as it is generally not polarized. The resultant extra luminescence is able to reach a detector. European Patent Application Serial No. 05198773.2, entitled "Luminescence Sensor Comprising at Least Two Wire Grids," filed on Sep. 22, 2005, combines two aperture grids positioned substantially perpendicular to one another. The combination of the aperture grids creates apertures with the advantages of the aperture biosensor while lacking the disadvantage of the apertures.

However, the biosensor in the above patent application is difficult to make robust at reasonable cost. Hence, there is a need in the industry for a biosensor that incorporates the advantages of the biosensor of the aforementioned application having a simpler design and a lower cost.

A method and sensor for the detection of luminescence radiation generated by at least one luminophore is disclosed. In the context of the present invention, a method and sensor for the detection of luminescence radiation generated by at least one luminophore is disclosed. In the context of the present invention the biosensor comprises a grid (120) defined as arrays of apertures with the apertures having a first dimension below and a second dimension above the diffraction limit of the excitation light (102) in a medium, a polarizer (115), and luminophores (117) positioned in a volume selected from the group consisting of: the volume inside the apertures of the grid (120), the volume in between the array of slits (120) and the polarizer (115) and a volume that extends into the polarizer (115), wherein the grid (120) providing a transmission axis extending in a first direction and the polarizer (115) providing a transmission axis extending in a second direction, the first direction and the second direction being substantially perpendicular with respect to each other, wherein the excitation radiation (102) is polarized such that it is substantially suppressed by one of the at least grid (120) and polarizer (115) and substantially not suppressed by the other of the at least grid (120) and polarizer (115).

Figure 3:
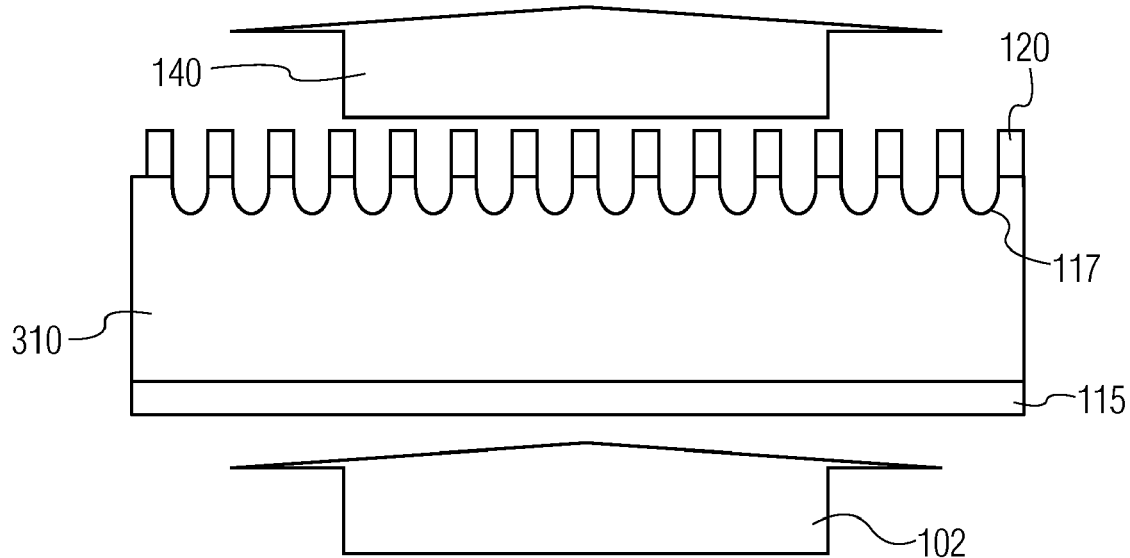
Figure 4:
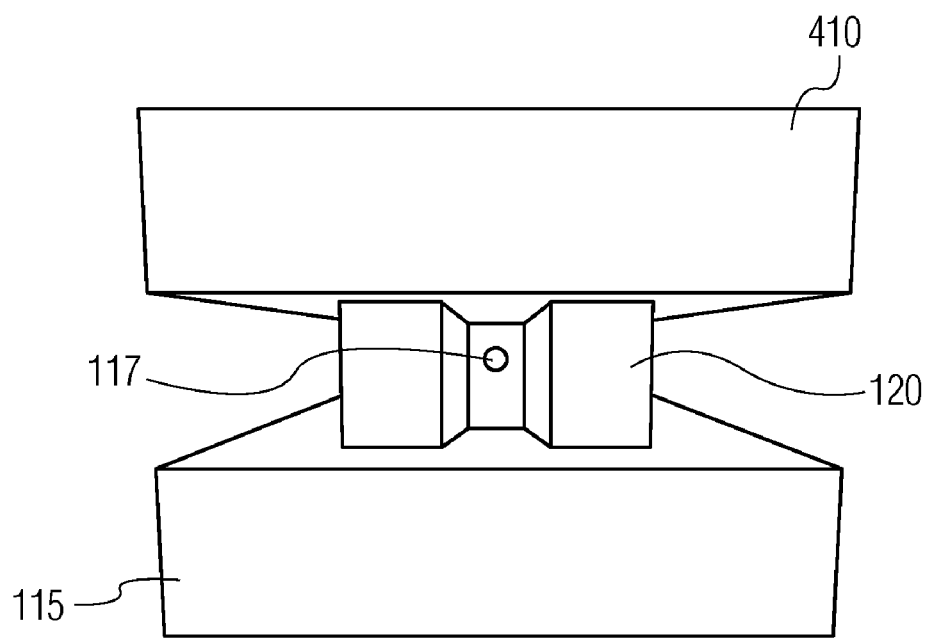
Figure 5:
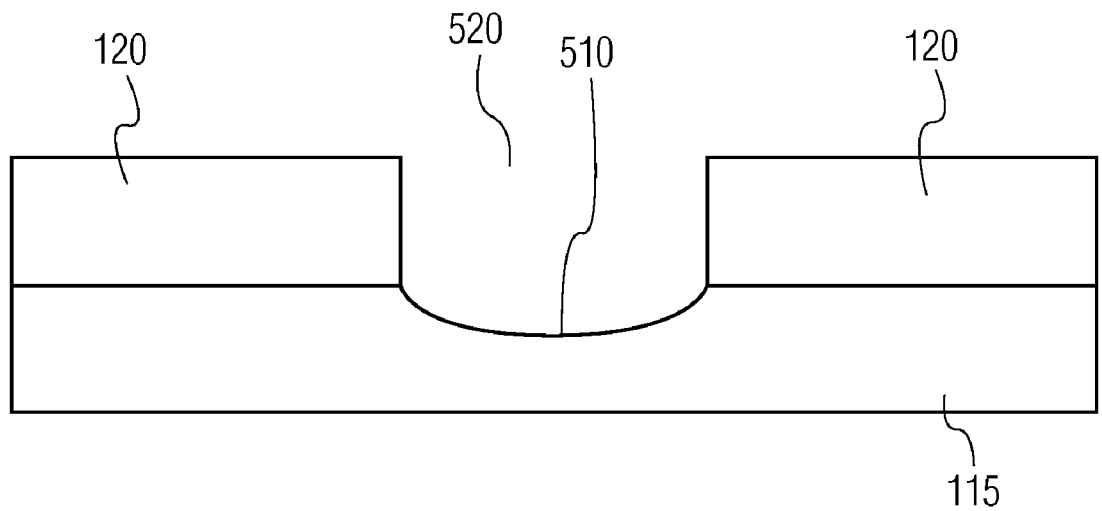

FIG. 3 illustrates a cross-sectional view of a third exemplary embodiment of a biosensor in accordance with the principles of the invention; and FIG. 4 illustrates a cross-sectional view of a fourth exemplary embodiment of a biosensor in accordance with the principles of the invention; and FIG. 5 illustrates a cross-section view of a fifth exemplary embodiment of a biosensor in accordance with the principles of the invention.

It is to be understood that these drawings are for purposes of illustrating the concepts of the invention and are not to scale. It will be appreciated that the same reference numerals, possibly supplemented with reference characters where appropriate, have been used throughout to identify corresponding parts.

The present invention will be described with respect to particular embodiments and with reference to certain drawings but the invention is not limited thereto only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Figure 1A:
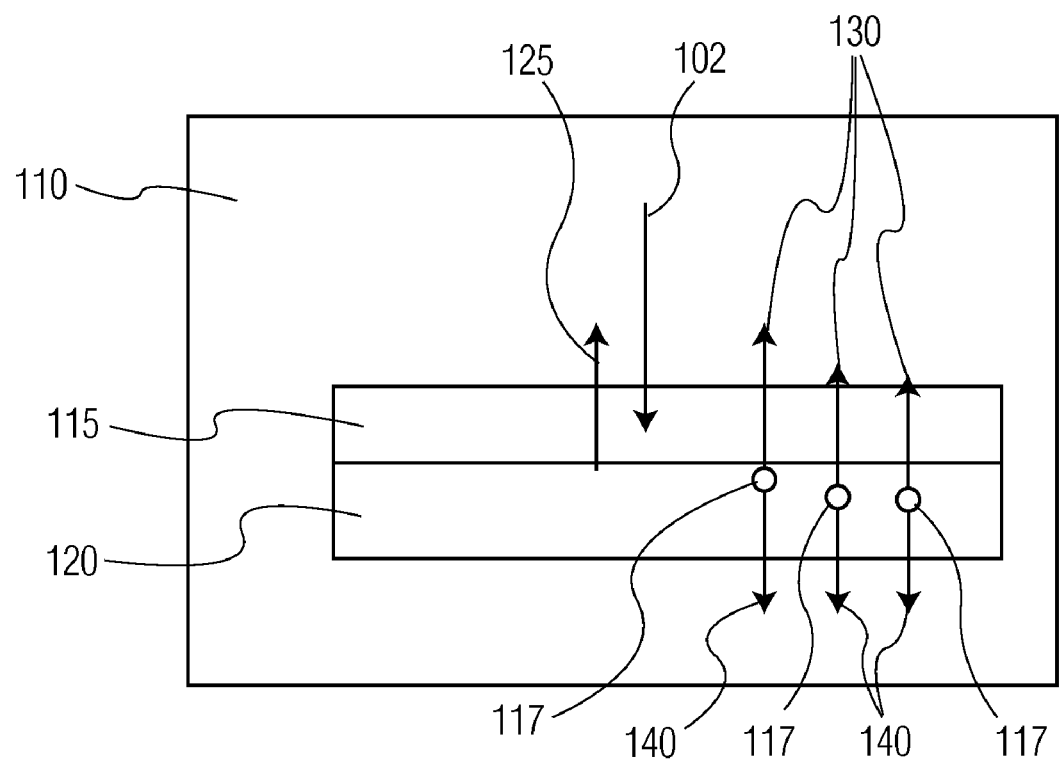
FIG. 1A illustrates a cross-sectional view of a first exemplary embodiment of a biosensor in accordance with the principles of the invention.

FIG. 1A illustrates a first exemplary embodiment of a biosensor 110 in accordance with the principles of the invention. In this exemplary embodiment excitation light 102 illuminates biosensor 110, which is composed of a polarizer 115 and an aperture grid 120. The polarizer 115 and aperture grid 120 are positioned or oriented such that their respective transmission axes are substantially perpendicular to each other.

In this exemplary embodiment excitation radiation or light 102 is polarized such that it is not suppressed by the polarizer 115 but is suppressed by aperture grid 120. When the suppression of radiation 102 is achieved by reflection, the resultant reflected beam 125 is directed away from aperture grid 120. Luminophores 117 are contained between polarizer 115 and aperture grid 120. In one embodiment the luminophores 117 are preferably adhered to the aperture grid 120. In still another embodiment, luminophores 117 are adhered to the surface of polarizer 115 facing aperture grid 120. As would be recognized, the molecules that are of interest are conventionally labeled with a luminophore and adheres to specific capture molecules that are present on the surface. Alternatively, adhered targets are detected with a secondary capture molecule that is labeled with a luminophore and adheres to immobilized targets or adheres to the fraction unbound capture molecule. The luminophores themselves are indirectly attached via the adhered targets or detection molecules. Luminophores may be organic fluorophores, quantum dots, chemiluminescent molecules, or electroluminescent molecules.

When energy from light 102 strikes luminophores 117, luminescence is generated in an omni pattern and only a portion of the light is directed to aperture grid 120 and a portion is directed toward polarizer 115. This is illustrated by the two beams 130 and 140, respectively, in the plane of FIG. 1A. In this case beam 140 will encounter aperture grid 120 and be passed to a detector (not shown). In one aspect of the invention, when polarizer 115 is a dichroic polarizer, beam 130 may be partly absorbed and partly transmitted by polarizer 115. In another aspect of the invention, when polarizer 115 is a birefringent stack polarizer, beam 130 may be partly reflected and partly transmitted. In the case, the partly reflected beam 130 enhance the signal strength of beam 140.

The aperture grid 120 and polarizer 115 may be selected as dichroic polarizers based on an oriented polarization dependent absorber. For example, a polyvinylalcohol material may be modified with a diachronic dye or iodine crystals to achieve the desired characteristics. A smectic polarizer, as discussed in U.S. patent application Ser. No. 10/578,062, now U.S. Pat. No. 7,763,330 can be used to produce a very thin film, in the order of 2 to 6 micrometers on a substrate. As it is densely crosslinked it is accessible for further processing steps such as lithographic steps to produce a grid polarizer. Alternatively, polarizer 115 may be a reflecting polarizer, e.g., DBEF polarizer. Such polarizers are well-known in the art and need do be discussed herein. See for example, U.S. Pat. Nos. 5,094,788; 5,122,905; and 5,122,906.

Figure 1B:
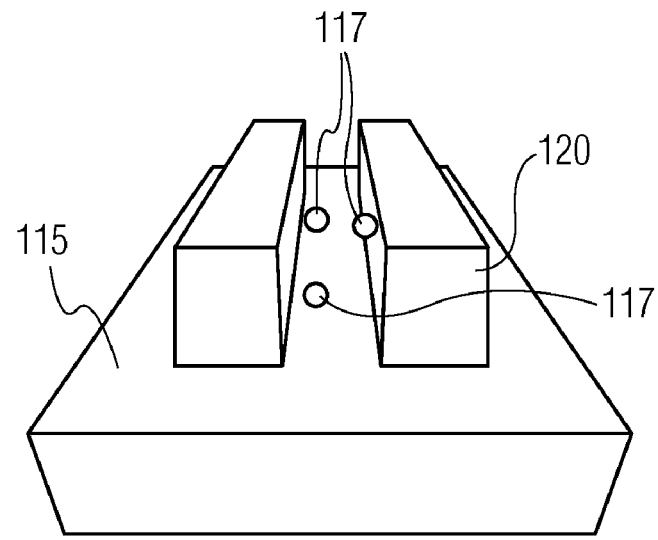
FIG. 1B illustrates a prospective view of the biosensor shown in FIG. 1A.

FIG. 1B illustrates a prospective view of biosensor 110 shown in FIG. 1A. In this illustrated view the preferred locations of luminophores 117 are shown. Further illustrated is that aperture grid 120 is composed of apertures (slots, slits) with a second dimension (above the diffraction limit) significantly larger (here drawn as extending from −infinity to +infinity) than the first dimension (below the diffraction limit).

Figure 1C:
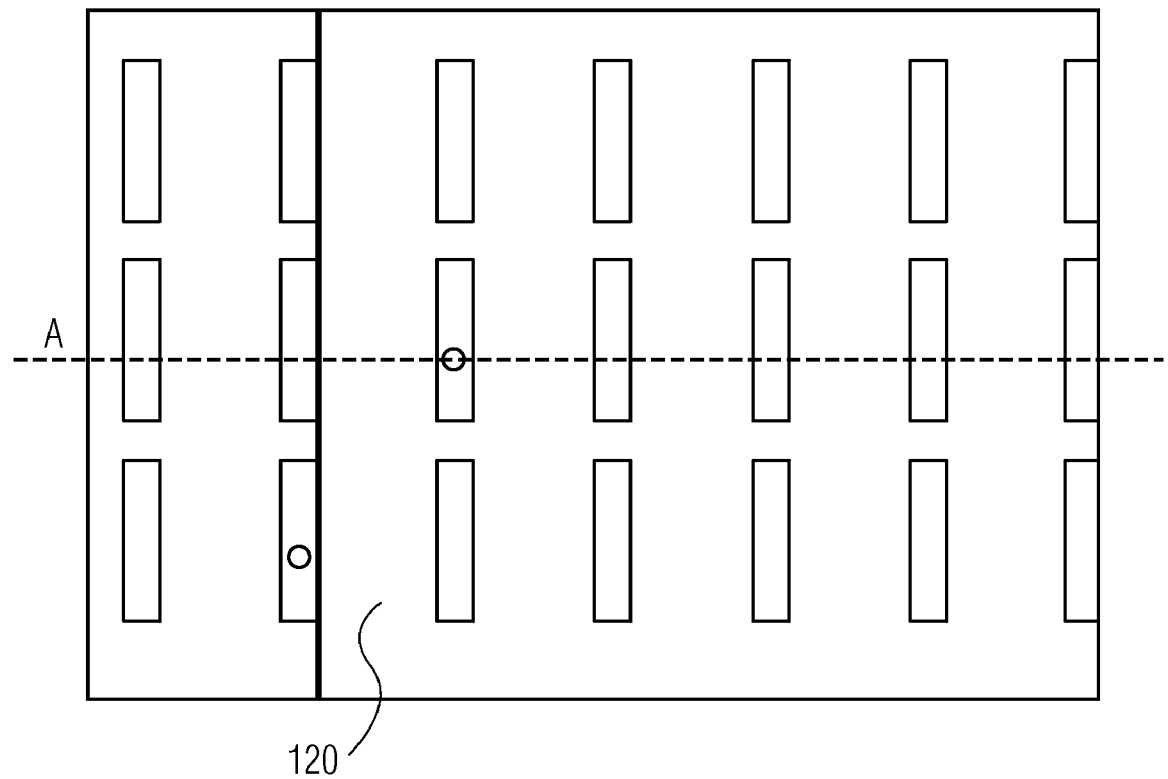
FIG. 1C illustrates a top view of a biosensor in accordance with the principles of the invention.

FIG. 1C illustrates a top view of a biosensor in accordance with the principles of the present invention. In this illustrated view, an aperture grid 120 is composed of a plurality of apertures having rectangular shape. Each aperture has a first dimension significantly smaller than a second direction. In this case, the first dimension is selected to be below the diffraction limit of the excitation light (102), while the second dimension is selected to be above the diffraction limit of the excitation light (102).

Figure 1D:
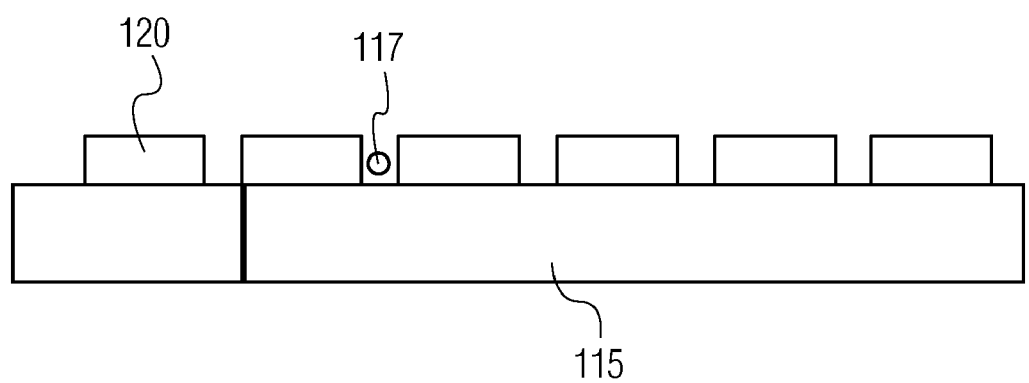
FIG. 1D illustrates a cross-sectional view (through section A-A) of the biosensor shown in FIG. 1C.

FIG. 1D illustrates a cross-section view, through section A-A, of the aperture grid shown in FIG. 1C. This view illustrates how apertures are etched into the material to form aperture grid 120. Also shown is luminophores 117 located in the volume of the apertures.

Figure 2:
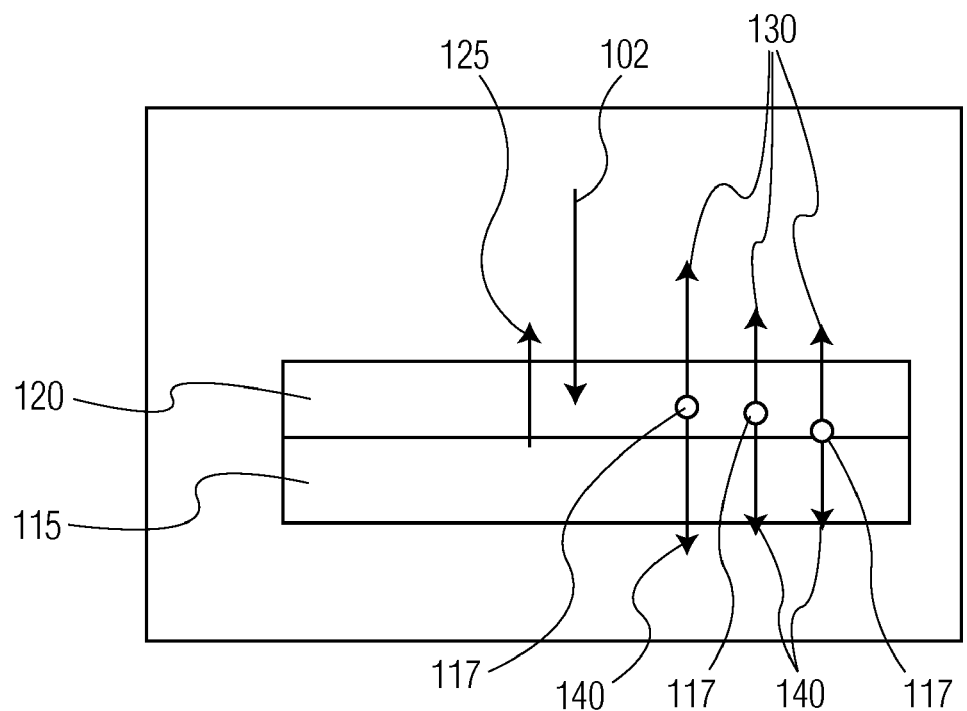
FIG. 2 illustrates a cross sectional view of a second exemplary embodiment of a biosensor in accordance with the principles of the invention.

FIG. 2 illustrates a second exemplary embodiment of the invention. In this illustrated case, the location of aperture grid 120 and polarizer 115 are switched and excitation light 102 is suppressed by polarizer 115. Luminophores 117 are included between aperture grid 120 and polarizer 115, as previously discussed, and in this example, adhered on, or very close to the surface of polarizer 115.

The excitation volume (i.e., the volume where the intensity of the excitation light is sufficiently high for the generation of appreciable luminescence) is determined by the rate of absorption in polarizer 115. The advantage of this is that the emitted luminescence is increased due to light reflecting from the aperture grid 120 towards the detector.

In one aspect of the invention, whether with the embodiment shown in FIG. 1A or FIG. 2, a dichroic dye that may be used for polarizer 115 may have a narrow absorption band. This absorption band may be chosen such that it absorbs energy at the wavelength of the excitation light 102 but transmits at the wavelength of the emitted beam 140. In this case the intensity of beam 140 may be further enhanced.

In another aspect of the invention, the polarizer layer 115 may consist of a quarterwave film, optimized for the wavelength of the excitation light 102 and a film consisting of a cholesteric network. The cholesteric network selectively reflects the non-used part of the beam 102 and transmits all emitted light 140 in addition to part of the reflected light 130. The advantage of the cholesteric network is that it has a very steep reflection band thus enabling discrimination between the excitation and the luminescence wavelengths.

FIG. 3 illustrates a third exemplary embodiment of the present invention wherein a glass plate 310 is introduced between polarizer 115 and aperture grid 120.

FIG. 4 illustrates a fourth exemplary embodiment of the present invention wherein a glass plate 410 is introduced in contact with aperture grid 120. In this case, the aperture grid 120 is sandwiched between (at least) polarizer 115 and glass-plate 410 and forms flow channels by which luminophores 117 may be introduced in the volume between the slots of aperture grid 120.

FIG. 5 illustrates another exemplary embodiment of the present invention wherein polarizer 115 is etched in the region corresponding to the slots 520 of aperture grid 120. This embodiment of the invention is advantageous as the extra volume 510 created by the etching has full excitation power and can be tuned by varying the depth of the etching.

In another aspect of the invention, (not shown) additional filtering devices, such as a polarizer and/or additional bandpass filters, may be incorporated selectively included. The additional polarizer and/or bandpass filters may be used to suppress background light or filter both the excitation and emission wavelengths.

While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention.

It is expressly intended that all combinations of those elements that perform substantially the same function in substantially the same way to achieve the same results are within the scope of the invention. Substitutions of elements from one described embodiment to another are also fully intended and contemplated.

The invention claimed is:

1. A luminescence sensor, comprising:
   a grid defined as arrays of apertures with the apertures having a first dimension below a diffraction limit of an excitation light and a second dimension above the diffraction limit of the excitation light in a medium;
   a polarizer; and
   luminophores positioned in a volume selected from the group consisting of: a volume inside an aperture of the grid, a volume in between the array of apertures and the polarizer, and a volume that extends into the polarizer, wherein the grid provides a transmission axis extending in a first direction and the polarizer provides a transmission axis extending in a second direction, the first direction and the second direction being substantially perpendicular with respect to each other.

2. The sensor according to claim 1, further comprising:
   a glass plate between the polarizer and the grid.

3. The sensor according to claim 1, further comprising:
   a glass plate in contact with the grid.

4. The sensor according to claim 1, further comprising:
   a plurality of areas etched into the polarize, the areas corresponding to the apertures in the grid.

5. The sensor according to claim 4, wherein the depth of etching is variable.

6. The sensor according to claim 1, wherein, when the sensor is irradiated with excitation radiation, the excitation radiation is polarized such that it is substantially suppressed by one of the grid and the polarizer and substantially not suppressed by the other of the grid and the polarizer.

7. The sensor according to claim 6, wherein the excitation radiation is polarized such that it is substantially suppressed by the polarizer which is positioned farthest away from a source of the excitation radiation and substantially not suppressed by the grid which is positioned closest to the source of the excitation radiation.

8. The sensor according to claim 1, the polarizer having a top surface, wherein the grid is positioned on the top surface of the polarizer.

9. The sensor according to claim 1, wherein the polarizer has an absorption band that absorbs energy at a known wavelength.

10. The sensor according to claim 1, wherein the polarizer is a quarterwave film and a cholesteric network.

11. A method comprising:
    irradiating a luminescence sensor with excitation radiation, wherein the luminescence sensor comprises:
      a grid defined as arrays of apertures, with the apertures having a first dimension below and a second dimension above a diffraction limit of the excitation light in a medium;
      a polarizer; and
      luminophores positioned in a volume selected from the group consisting of: a volume inside the apertures of the grid, a volume in between the array of apertures and the polarizer, and a volume that extends into the polarizer, wherein the grid provides a transmission axis extending in a first direction and the polarizer provides a transmission axis extending in a second direction, the first direction and the second direction being substantially perpendicular with respect to each other, wherein the excitation radiation is polarized such that it is substantially suppressed by one of the grid and the polarizer and substantially not suppressed by the other of the grid and polarizer.

12. The method according to claim 11, wherein the excitation radiation is not substantially suppressed by the grid but is substantially suppressed by the polarizer.

13. The method according to claim 11, further comprising detecting the generated luminescence radiation.

14. The method according to claim 11, wherein the sensor further comprising:
    a glass plate (310) between the polarizer (115) and the grid (120).

15. The method according to claim 11, wherein the sensor further comprises:
    a glass plate in contact with the grid.

16. The method according to claim 11, wherein the sensor further comprises:
    a plurality of areas etched into the polarizer, the areas corresponding to the slots in the grid.

17. The sensor according to claim 1, further comprising:
    a filtering device selected from the group consisting of: a polarizing beam splitter and a band-pass filter.

18. The method according to claim 11, wherein the luminescence sensor further comprises:
    a filtering device selected from the group consisting of: a polarizing beam splitter and a band-pass filter.

* * * * *